(12) United States Patent
Blanchard (10) Patent No.: US 7,681,577 B2
(45) Date of Patent: Mar. 23, 2010

(54) EAR TIP

(75) Inventor: Mark A. Blanchard, Lebanon, IN (US)

(73) Assignee: Klipsch, LLC, Indianapolis, IN (US)

( * ) Notice: Subject to any disclaimer, the term of this patent is extended or adjusted under 35 U.S.C. 154(b) by 284 days.

(21) Appl. No.: 11/584,862

(22) Filed: Oct. 23, 2006

(65) Prior Publication Data

US 2008/0187159 A1    Aug. 7, 2008

(51) Int. Cl.
| | |
|---|---|
| A61F 5/37 | (2006.01) |
| A61F 11/00 | (2006.01) |
| H04R 25/00 | (2006.01) |
| H04R 25/02 | (2006.01) |
| A61B 7/02 | (2006.01) |
| A61F 11/06 | (2006.01) |
| A61N 1/00 | (2006.01) |

(52) U.S. Cl. ............... 128/864; 381/71.1; 381/71.6; 381/380; 181/128; 181/129; 181/130; 181/134; 181/135; 600/25; 607/55; 607/56; 607/57; 128/846; 128/857

(58) Field of Classification Search ............... 128/846, 128/857, 864; 181/128–135; 381/71.1, 71.6, 381/380; 600/25; 607/55–57
See application file for complete search history.

(56) References Cited

U.S. PATENT DOCUMENTS

| | | |
|---|---|---|
| 789,876 A | 5/1905 | Pape |
| 1,556,775 A | 10/1925 | Fensky |
| 2,246,737 A | 6/1941 | Knudsen |
| 2,430,229 A | 11/1947 | Kelsey |
| 2,478,038 A | 11/1949 | Baum |
| 2,487,038 A | 11/1949 | Baum |
| 2,521,414 A | 9/1950 | Schier |
| 2,719,523 A | 10/1955 | Von Gierke |
| 2,987,584 A | 6/1961 | Webber |

(Continued)

FOREIGN PATENT DOCUMENTS

EP        0 567 706        10/1992

(Continued)

OTHER PUBLICATIONS

International Preliminary Report on Patentability and Written Opinion of the International Searching Authority, PCT/US07/10723—(related application).

*Primary Examiner*—Loan H Thanh
*Assistant Examiner*—Tarla R Patel
(74) *Attorney, Agent, or Firm*—Krieg DeVault LLP

(57) ABSTRACT

An improved ear tip for earphones and hearing protection is provided where comfort and occlusion of the ear are of most importance. The ear tip comprises an elastomer polymer resin material molded to form the material to the shape of the ear canal. A chamber is defined having a proximal and distal end, the distal end engages the acoustic exit of the transducer, sound source or sound attenuator and the proximal end of the bore is adapted to be disposed adjacent an eardrum. The inner body attaches to a nozzle, or audio playback orifice to naturally transition the acoustics from the transducer or sound attenuator to the eardrum via the ear canal. The ear tip can have a plurality of flexible annular flanges disposed at spaced intervals of the body with decreasing circumference as the flanges transition to the proximal end. Each flange tapers in a radius or curvilinear geometry as it progresses to the end of the object.

14 Claims, 7 Drawing Sheets

Major Axis

Minor Axis

U.S. PATENT DOCUMENTS

| | | | |
|---|---|---|---|
| 3,061,689 A | 10/1962 | McCarrell et al. | |
| 3,080,011 A | 3/1963 | Henderson | |
| D207,216 S | 3/1967 | Geib | |
| RE26,258 E | 8/1967 | Martin | |
| 3,414,685 A | 12/1968 | Geib et al. | |
| 3,548,118 A | 12/1970 | Hutchings | |
| 3,610,841 A | 10/1971 | Hutchings | |
| 3,618,697 A * | 11/1971 | Littmann et al. | 181/135 |
| 3,692,958 A | 9/1972 | Dymoke | |
| 3,865,998 A | 2/1975 | Weis | |
| 3,993,879 A | 11/1976 | Larkin | |
| 4,006,321 A | 2/1977 | Carlson | |
| D245,202 S | 7/1977 | Asker | |
| 4,039,765 A | 8/1977 | Tichy et al. | |
| 4,122,841 A | 10/1978 | Rock et al. | |
| 4,261,432 A | 4/1981 | Gunterman | |
| D259,279 S | 5/1981 | Takeda | |
| 4,325,453 A | 4/1982 | Moussette | |
| 4,335,281 A | 6/1982 | Scott et al. | |
| 4,347,911 A | 9/1982 | Bertagna et al. | |
| 4,548,082 A | 10/1985 | Engebretson et al. | |
| 4,677,675 A | 6/1987 | Killion et al. | |
| 4,764,168 A | 8/1988 | Suh | |
| D298,356 S | 11/1988 | Falco | |
| 4,870,688 A | 9/1989 | Voroba et al. | |
| 4,875,233 A | 10/1989 | Derhaag et al. | |
| 4,913,259 A | 4/1990 | Packard | |
| 4,936,411 A | 6/1990 | Leonard | |
| 5,031,219 A | 7/1991 | Ward et al. | |
| D330,761 S | 11/1992 | Falco | |
| 5,188,123 A | 2/1993 | Gardner, Jr. | |
| 5,201,007 A | 4/1993 | Ward et al. | |
| 5,288,953 A | 2/1994 | Peart | |
| 5,295,193 A | 3/1994 | Ono | |
| 5,298,692 A | 3/1994 | Ikeda et al. | |
| D353,379 S | 12/1994 | Nakamura et al. | |
| 5,487,012 A | 1/1996 | Topholm et al. | |
| 5,692,059 A | 11/1997 | Kruger | |
| 5,712,453 A | 1/1998 | Bungardt et al. | |
| 5,781,638 A | 7/1998 | Hosaka et al. | |
| 5,824,968 A * | 10/1998 | Packard et al. | 181/131 |
| 5,917,918 A | 6/1999 | Callahan | |
| 5,957,136 A | 9/1999 | Magidson et al. | |
| 5,979,589 A | 11/1999 | Aceti | |
| D427,304 S | 6/2000 | Magidson et al. | |
| 6,175,633 B1 | 1/2001 | Morrill et al. | |
| 6,205,227 B1 | 3/2001 | Mahoney et al. | |
| 6,253,871 B1 | 7/2001 | Aceti | |
| 6,258,043 B1 | 7/2001 | Raviv et al. | |
| 6,359,993 B2 | 3/2002 | Brimhall | |
| D468,300 S | 1/2003 | Boesen | |
| D468,721 S | 1/2003 | Nguyen | |
| 6,513,621 B1 | 2/2003 | Deslauriers et al. | |
| 6,532,295 B1 | 3/2003 | Brimhall et al. | |
| D473,652 S | 4/2003 | Darley et al. | |
| 6,574,345 B1 | 6/2003 | Huang | |
| 6,643,378 B2 | 11/2003 | Schumaier | |
| 6,648,813 B2 | 11/2003 | Zilberman et al. | |
| 6,688,421 B2 | 2/2004 | Dyer et al. | |
| 6,695,093 B1 | 2/2004 | Falco | |
| 6,751,327 B1 * | 6/2004 | Urso et al. | 381/323 |
| D499,397 S | 12/2004 | Hlas et al. | |
| 6,920,228 B2 | 7/2005 | Redmer et al. | |
| 6,920,229 B2 | 7/2005 | Boesen | |
| 6,940,988 B1 | 9/2005 | Shennib et al. | |
| D517,054 S | 3/2006 | Yang | |
| 7,010,137 B1 | 3/2006 | Leedom et al. | |
| 7,072,476 B2 | 7/2006 | White et al. | |
| 7,079,662 B2 | 7/2006 | Niederdrank | |
| 7,082,206 B2 | 7/2006 | Mahoney et al. | |
| 7,092,543 B1 | 8/2006 | Mahoney et al. | |
| 7,123,733 B1 | 10/2006 | Borowsky et al. | |
| D535,644 S | 1/2007 | Drambarean et al. | |
| 7,185,655 B1 * | 3/2007 | Redon | 128/864 |
| D542,773 S | 5/2007 | Drambarean et al. | |
| 7,221,768 B2 | 5/2007 | Sjursen et al. | |
| D549,222 S | 8/2007 | Yuang | |
| D550,201 S | 9/2007 | Drambarean et al. | |
| D550,655 S | 9/2007 | Falco | |
| D550,657 S | 9/2007 | Gan et al. | |
| D563,945 S | 3/2008 | Johns et al. | |
| D565,022 S | 3/2008 | Belliveau et al. | |
| D567,217 S | 4/2008 | Kamo et al. | |
| D569,842 S | 5/2008 | Yang | |
| D575,767 S | 8/2008 | Lee | |
| D575,773 S | 8/2008 | Yanai | |
| D579,006 S | 10/2008 | Kim et al. | |
| 2002/0058881 A1 | 5/2002 | Raviv et al. | |
| 2002/0076057 A1 | 6/2002 | Voix | |
| 2003/0159878 A1 * | 8/2003 | Hakansson et al. | 181/135 |
| 2003/0172938 A1 * | 9/2003 | Falco | 128/864 |
| 2004/0047481 A1 | 3/2004 | Bauman | |
| 2004/0240691 A1 | 12/2004 | Grafenberg | |
| 2005/0018838 A1 | 1/2005 | Meunier et al. | |
| 2005/0111687 A1 | 5/2005 | Lederer | |
| 2005/0165460 A1 | 7/2005 | Erfan | |
| 2006/0050912 A1 | 3/2006 | Kidd et al. | |
| 2006/0050916 A1 | 3/2006 | Wehner | |
| 2006/0147072 A1 | 7/2006 | Sodoma | |
| 2006/0159297 A1 | 7/2006 | Wirola | |

FOREIGN PATENT DOCUMENTS

| | | |
|---|---|---|
| EP | 1 681 904 | 1/2005 |
| EP | 1 578 168 | 7/2005 |
| GB | 2 373 667 | 12/2000 |
| JP | 10023578 | 6/1996 |
| JP | 20210327 | 6/1999 |
| WO | WO 97/37593 | 4/1997 |
| WO | WO 99/04601 | 7/1998 |
| WO | WO 01/08443 | 7/2000 |
| WO | WO 2004/077924 | 3/2004 |
| WO | WO 2005/025268 | 3/2005 |
| WO | WO 2005/112503 | 5/2005 |
| WO | WO 2006/068772 | 6/2006 |

* cited by examiner

Figure 1

Major Axis

Figure 2

Minor Axis

Major Axis

EAR TIP

The inventions disclosed and claimed herein are ear tips that come in contact with the ear canal wall, adapted for use with earphones, stethoscopes, perytympanic hearing instruments (hearing aids), headsets, and ear plugs for hearing protection, and more particularly "in ear" applications. The devices to which the ear tips can be operatively attached are generally known in the art, including earphones that can be positioned on the head or over the ear, in the ear and wires capable of operatively connecting the ear tip to an audio source such as an analog or digital audio player. Alternative uses include operative attachment to stethoscopes, hearing aids, headsets, and as ear plugs.

DETAILED DESCRIPTION OF REPRESENTATIVE EMBODIMENTS

For the purpose of promoting an understanding of the principles of the invention, reference is now made to the embodiments illustrated in the drawings and specific language is used to describe the same. No limitation of the scope of the invention is intended. Alterations and modifications to the illustrated devices, and other applications of the principles of the invention as illustrated herein are contemplated as would normally occur to one skilled in the art to which the invention relates.

Figure 1:
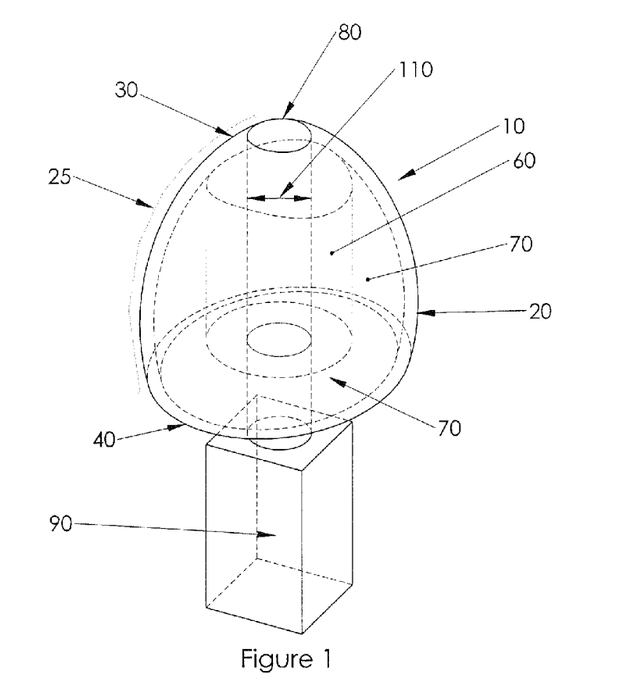
FIG. 1 shows a perspective view of one embodiment of an ear tip.
Figure 2:
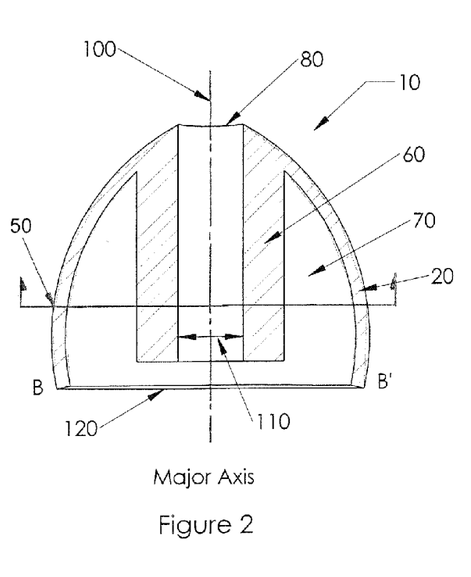
FIG. 2. shows a longitudinal cross-section of the ear tip shown in FIG. 1 taken along the major axis.
Figure 3:
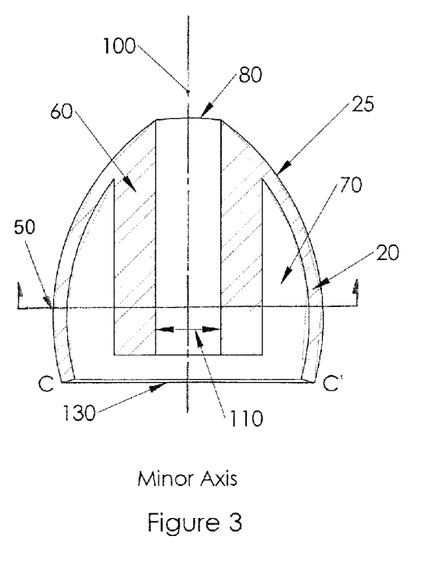
FIG. 3 shows a longitudinal cross-section of the ear tip shown in FIG. 1 taken along the minor axis.

As shown in FIGS. 1 and 2, the ear tip 10 has an annular flange 20 having a first end 30, a second end 40, at least a partially non-circular cross section 50 (shown for example in FIGS. 2 and 3). An inner body 60 extends from the first end 30 toward the second end 40 within a chamber 70. An acoustic channel 80 extends through the inner body 60 to connect operatively the sound source or sound attenuator 90 to the ear drum (not shown).

An inner body 60 is formed as part of the flange 20. The inner body 60 is positioned so that its longitudinal axis is generally concentric with the longitudinal axis of the flange 20 (i.e. along axis 100 as shown on FIGS. 2 and 3). The acoustic channel 80 extends through the inner body 60 and the first end 30. A transducer (not shown) may be positioned within or without the chamber 70. The inner body 60 may be formed integrally with the flange 20 or as a separate piece which is then attached to the flange 20.

The inner diameter 110 of the acoustic channel 80 is sized to secure an acoustic connection from a sound source or sound attenuator 90. The acoustic channel 80 in one version has a diameter of about 1.26 millimeters. In another version, the acoustic channel 80 has a diameter of about 1.40 millimeters. Variations to the diameter of the acoustic channel 80 can be made without varying from the scope of the invention disclosed and claimed herein.

The exterior surface 25 of the flange 20 tapers to the first end 30 from the second end 40. The arc of the taper can be constant or variable. In one version the radius is 5 millimeters. In another version, the radius is 9 millimeters. In other embodiments, the flange 20 has a generally conical three-dimensional shape. Again, variations in the arc or radius of the taper can be made without varying from the scope of the invention disclosed and claimed herein.

Referring to FIGS. 2 and 3, the ear tip 10 has a major axis 120 along B-B' and minor axis 130 along C-C'. The major axis 120 is longer than the minor axis 130. The minor axis 130 has a length from about 6 millimeters to about 10 millimeters. The major axis 120 has a length from about 9 millimeters to about 15 millimeters. The ratio of the length of the major axis 120 relative to the minor axis 130 can range from about 1.1:1 to about 3:1. The lengths of the axes can be varied without departing from the scope of the inventions disclosed and claimed herein.

Figure 4:
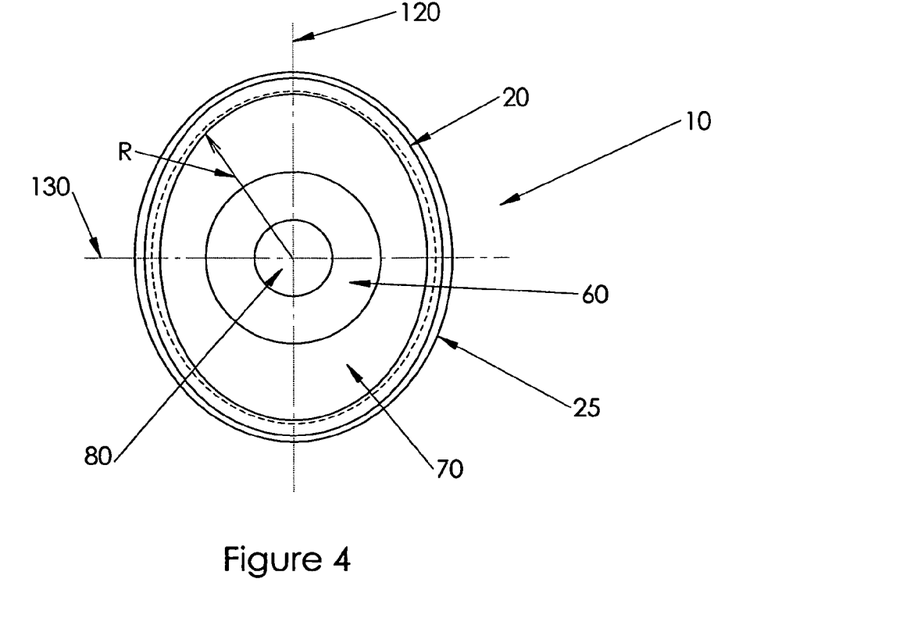
FIG. 4 shows a lateral cross-section of an embodiment having an elliptical cross-section.
Figure 5:
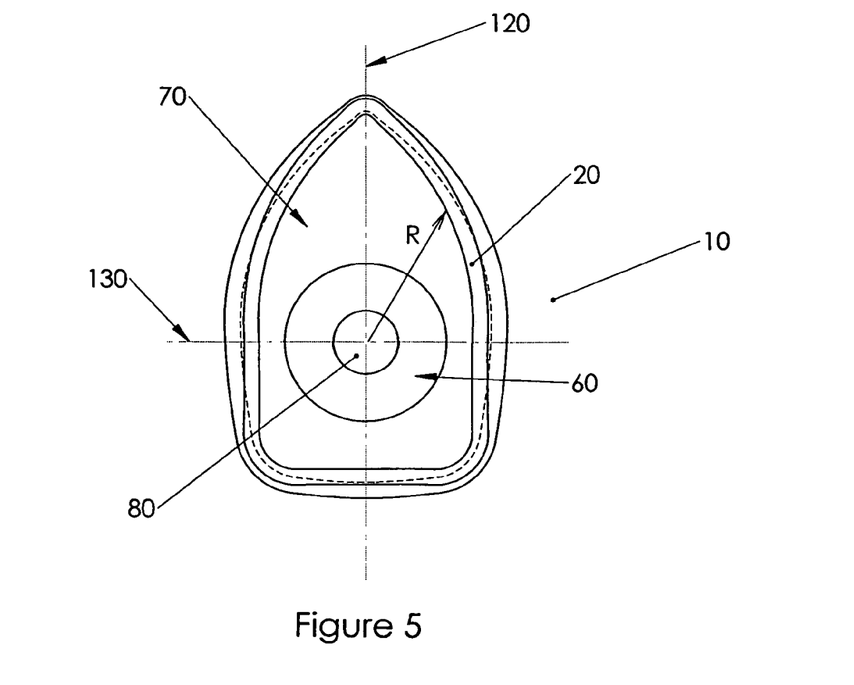
FIG. 5 shows a lateral cross-section of an embodiment having a generally triangular cross-section.
Figure 6:
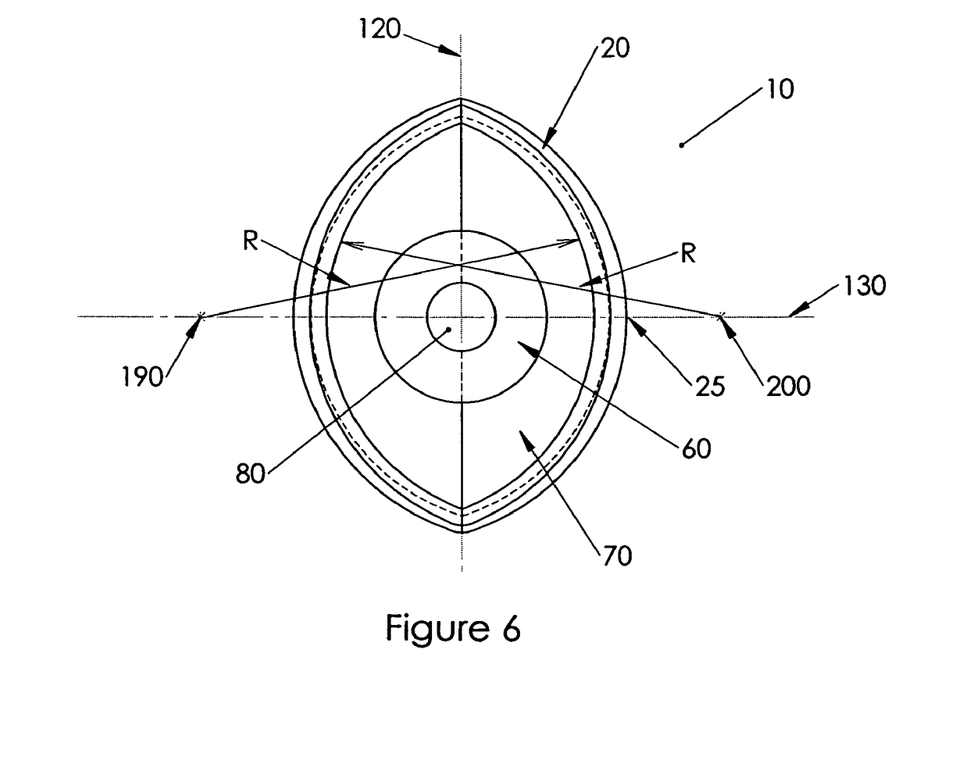
FIG. 6 shows a lateral cross-section of an embodiment having a clamshell shaped cross-section.

FIGS. 4-6 show several embodiments having different shaped lateral cross-sections. FIG. 4 shows a flange 20 having a generally elliptical cross-section 50. The major axis 120 and minor axis 130 are shown. Radius "R" will decrease as it arcs from the major axis 120 to the minor axis 130 according to known mathematical equations for ellipses $[(x^2/a^2)+(y^2/b^2)=1]$. One can infinitely vary the radius "R" or the generally elliptical shape of the inventions without departing from the scope thereof as disclosed and claimed.

FIG. 5 shows another embodiment with a flange 20 having a generally triangular shaped lateral cross-section. This generally triangular shaped lateral cross-section can also be referred to as a tri-oval shape. The inner body 60 defines an acoustic channel 80. Taken from the axis of the acoustic channel 80, radius R varies in length as it arcs from the minor axis 130 to the major axis 120. Sections of the cross-section can have generally non-radial lineal geometries in varying length (FIG. 5).

FIG. 6 shows another embodiment with a flange 20 having a generally clamshell shaped lateral cross-section. This clamshell shape can be described as taking a longitudinal cross-section along the major axis 120 thereby separating the flange 20 into two halves having radii "R" based on center points 190, 200 outside the acoustic channel 80. Alternatively the center points 190, 200 can be inside the chamber 70 or acoustic channel 80. FIG. 5 shows another embodiment with a flange 20 having a generally triangular shaped lateral cross-section. This generally triangular shaped lateral cross-section can also be referred to as a tri-oval shape. The inner body 60 defines an acoustic channel 80. Taken from the axis of the acoustic channel 80, radius R varies in length as it arcs from the minor axis 130 to the major axis 120. Sections of the cross-section can have generally non-radial lineal geometries in varying length (FIG. 5).

FIG. 6 shows another embodiment with a flange 20 having a generally clamshell shaped lateral cross-section. This clamshell shape can be described as taking a longitudinal cross-section along the major axis 120 thereby separating the flange 20 into two halves having radii "R" based on center points 190, 200 outside the acoustic channel 80. Alternatively the center points 190, 200 can be inside the chamber 70 or acoustic channel 80.

Figure 7:
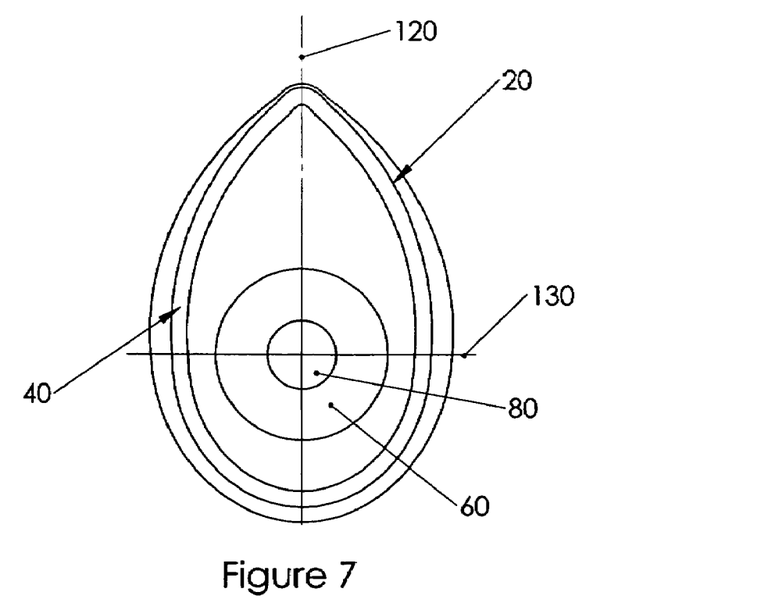
FIG. 7 shows a lateral cross-section of the ear tip having a teardrop cross-section.

Referring to FIG. 7, the flange 20 has a lateral cross-section having a generally teardrop shape. Alternatively, the lateral cross-section of the flange 20 can be generally oval, elliptical, or triangular (FIGS. 4 and 5). The flange 20 can have a cross-section having a substantially uniform arc as it extends from the minor axis 130 to the major axis 120. In another version, the flange 20 has a cross-section has a variable arc as it extends from the minor axis 130 to the major axis 120. In another variation, the flange 20 has a cross-section having a generally increasing radius as it extends from the minor axis 130 to the major axis 120.

Figure 8:
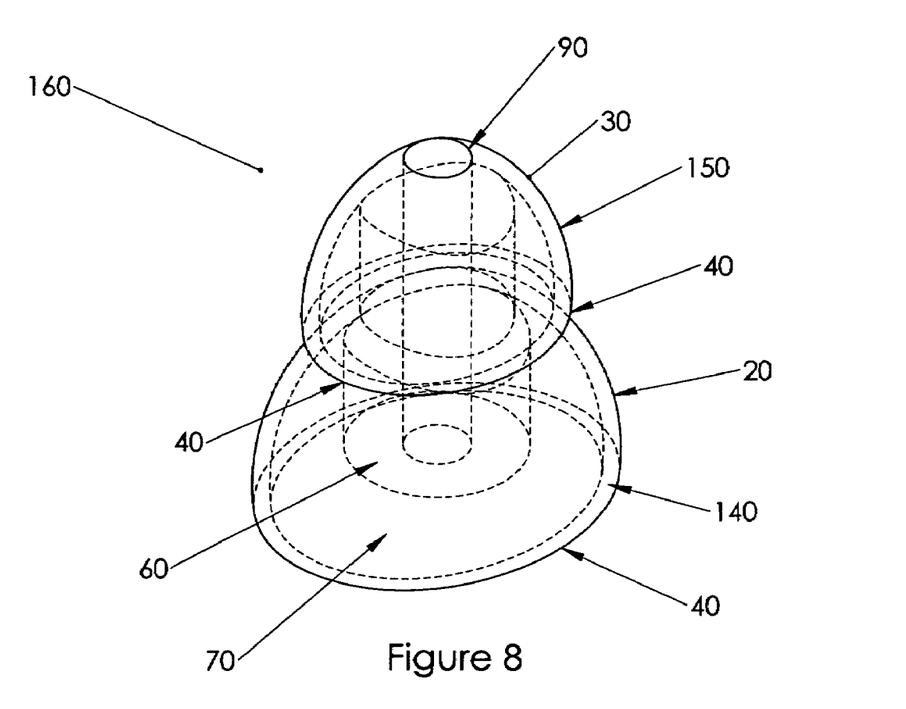
FIG. 8 shows a perspective view of another embodiment of the invention having two flanges.
Figure 9:
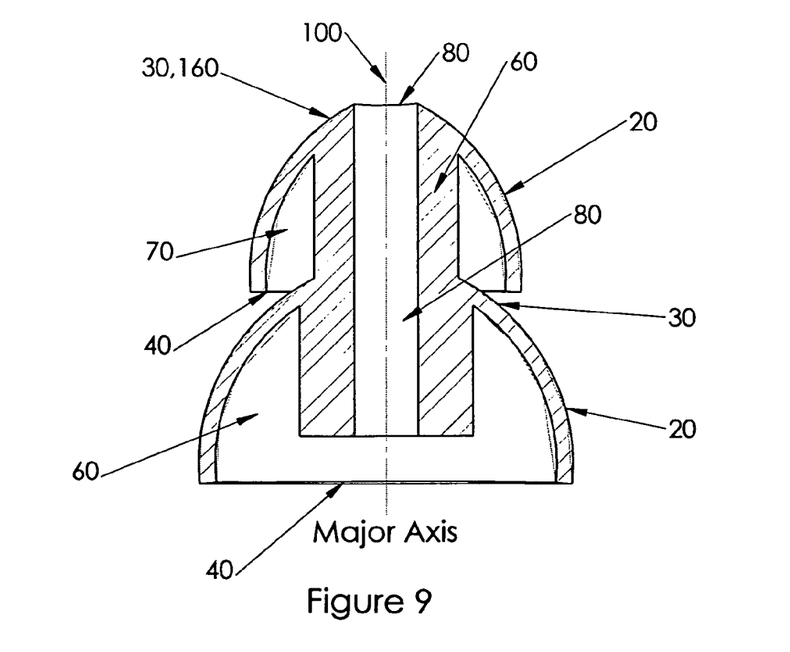
FIG. 9 shows a longitudinal cross-section of the embodiment shown in FIG. 5 taken along the major axis.
Figure 10:
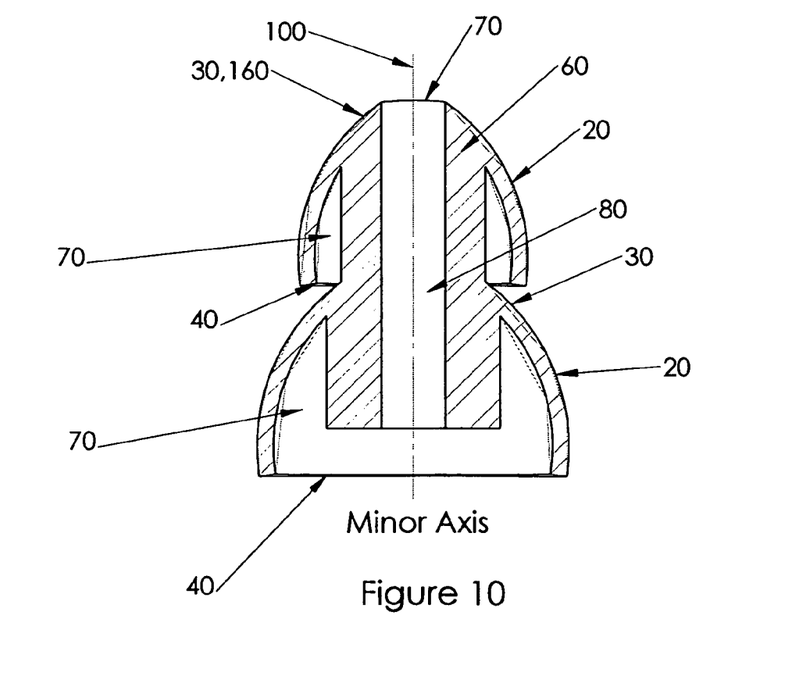
FIG. 10 shows a longitudinal cross-section of the embodiment shown in FIG. 5 taken along the minor axis.

Single flange ear tips 10 attenuate ambient noise by about 5 to about 15 dB. For additional noise isolation, multiple flanges 140, 150 can be used to yield attenuation up to about 32 dB. FIGS. 8-10 show a perspective view of an embodiment having a first flange 140 and a second flange 150 positioned along a common longitudinal axis (not shown). More than two flanges 140, 150 may be used without departing from the scope of the inventions disclosed and claimed.

The flanges 140, 150 have generally decreasing diameters as the flanges 140, 150 transition to an insertable end 160. The insertable end 160 is that portion of the ear tip 10 that is inserted the furthest into the ear canal. The flanges 140, 150 can be of single piece construction or multiple piece construction. For the embodiments having multiple flanges 140, 150, the inner body 60 can have an acoustic channel 80 extending through it. The inner body 60 traverses at least part of the length of both flanges 140, 150 as shown in FIG. 8-10. Each of the flanges 140, 150 has a first end 30 and a second end 40. At least one of the flanges 140, 150 has a partially non-circular cross section as described above with respect to the embodiment having a single flange 20. Each of the flanges 140, 150 defines a chamber 70.

Figure 11:
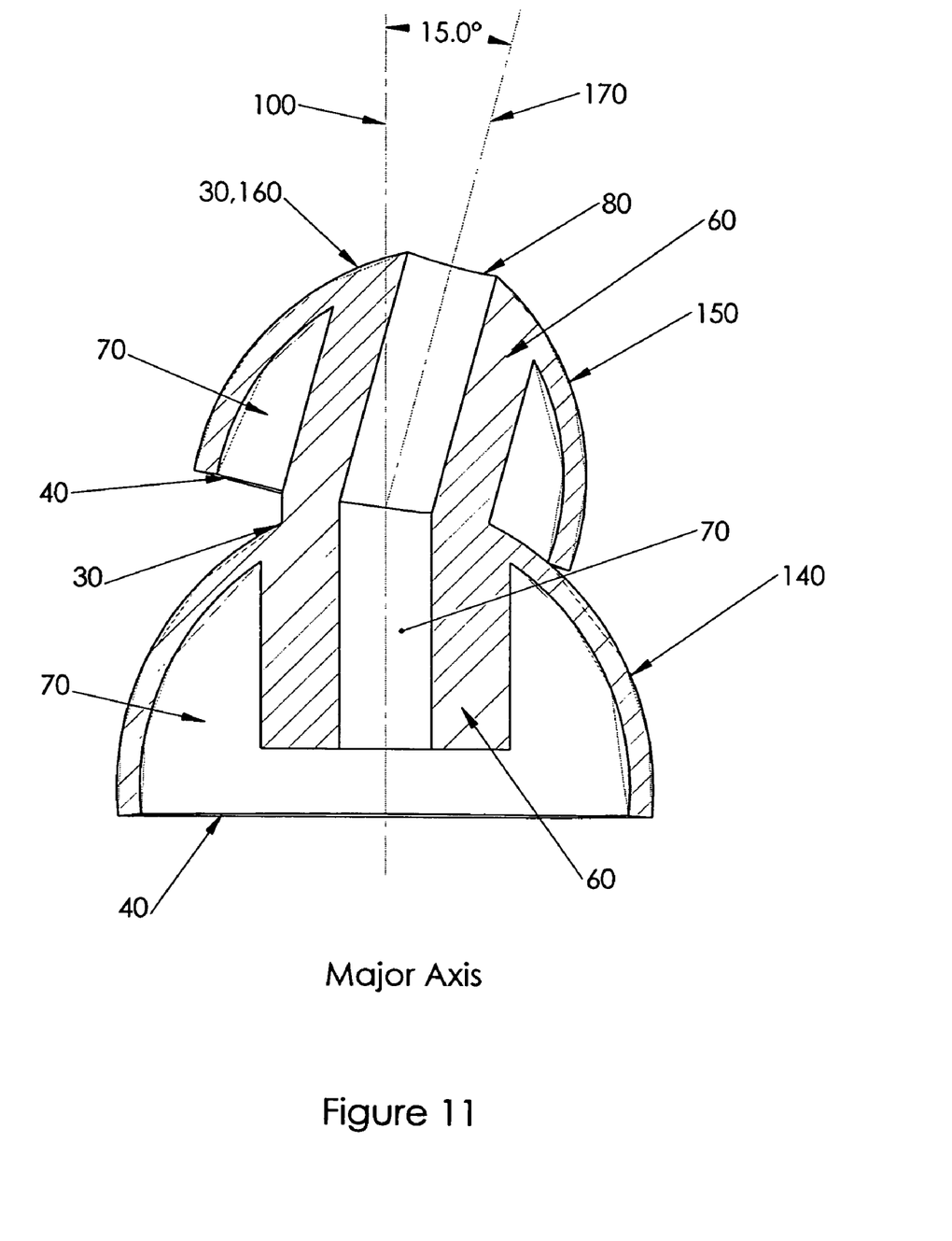
FIG. 11 shows another embodiment in which a first flange is positioned relative to a second flange at a 15° angle.

In one embodiment having two flanges (FIG. 11), the second flange 150 has a longitudinal axis 170 angled about 15 to about 30 degrees from the longitudinal axis 100 of flange 140. The deflection of the second flange 150 with respect to the first flange 140 can comprise a compound angle that is an angle of 15° in the x-axis and 15° in the y-axis or any combination thereof. Referring to FIGS. 9 and 10, in another embodiment, the longitudinal axis 100 of both flanges 140, 150 are common. In embodiments having multiple flanges 140, 150 (FIGS. 8-10), the flanges 140, 150 may have the same or different shaped lateral cross-sections, including oval, elliptical, triangular or teardrop shaped.

Rigid, deformable, flexible, elastic or resilient materials provide flexibility in sizing the ear bud, comfort, audio quality and durability. In one embodiment, the flange is a polymer. In another embodiment, the flange is an elastomeric polymer. In another embodiment the flange 20 is comprised of ABS plastic or polycarbonate plastic.

In single and multiple flange embodiments, the inner body 60 will have sufficient thickness and stiffness to resist deformation when it is connected to a sound source and when the ear tip 10 is inserted into an ear.

Figure 12:
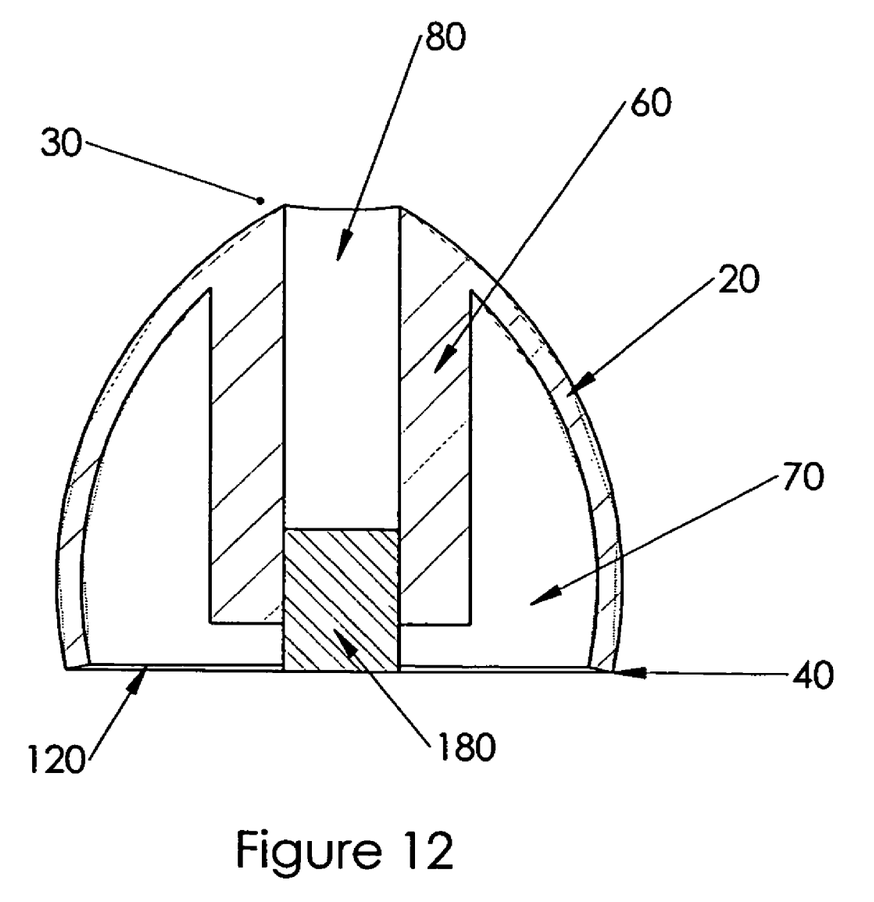
FIG. 12 shows a longitudinal cross-section of an embodiment having an insert.

As shown in FIG. 12, a removable or fixed insert 180 may be provided to plug the acoustic channel 80 thereby rendering the invention an ear plug. The insert 180 may be formed integrally with the inner body 60 to become either a homogeneous or non-homogeneous solid body.

The invention has been illustrated and described in detail in the drawings and foregoing description. The same is illustrative and not restrictive in character. Only the preferred embodiments have been shown and described. All changes and modifications that come within the spirit of the inventions are desired to be protected.

While the use of words such as preferable, preferably, preferred or more preferred utilized in the description indicate that the feature so described may be more desirable, such feature(s) may not be necessary. Embodiments lacking the same are within the scope of the invention as defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

I claim:

1. An ear tip comprising an annular flange having a first end and a second end, where the flange has a non-circular lateral cross section running from approximately the first end to the second end, the non-circular lateral cross-section has a major axis and a minor axis, the major axis having a greater length than the minor axis, the flange tapering to the first end from the second end, an inner body extending internally from the first end within a hollow interior defined by the flange toward the second end and terminating prior to reaching the second end, and an acoustic channel extending through the inner body, where the flange at least partially occludes an ear canal from ambient noise and creates at least a partial air seal in the ear canal and the acoustic channel is configured to allow the passage of sound into the ear canal when the inner body is connected with a sound source.

2. The ear tip of claim 1 wherein the ratio of the greater length of the major axis to the minor axis is from about 1.1:1 to about 3:1.

3. The ear tip of claim 1 wherein the cross-section has at least one substantially uniform arc as it extends from the minor axis to the major axis.

4. The ear tip of claim 1 wherein the cross-section has at least one variable arc as it extends from the minor axis to the major axis.

5. The ear tip of claim 1 wherein the cross-section has at least one generally increasing radius as it extends from the minor axis to the major axis.

6. The ear tip of claim 1 where the cross-section is elliptical.

7. The ear tip of claim 1 wherein the cross-section is generally triangular shaped.

8. The ear tip of claim 1 wherein the flange has a generally teardrop shaped cross-section.

9. The ear tip of claim 1 wherein the flange comprises a substantially rigid material.

10. The ear tip of claim 1 wherein the flange comprises a flexible material.

11. The ear tip of claim 1 wherein the flange comprises a deformable material.

12. The ear tip of claim 1 wherein the flange comprises an elastic material.

13. The ear tip of claim 1 wherein the flange comprises a resilient material.

14. The ear tip of claim 1 wherein the acoustic channel is sized to accept an insert to attenuate ambient noise from entering the acoustic channel.

* * * * *